(12) United States Patent
Korporaal

(10) Patent No.: US 10,610,169 B2
(45) Date of Patent: Apr. 7, 2020

(54) DETERMINING AN INITIALIZATION TIME POINT OF IMAGING USING A CONTRAST MEDIUM

(71) Applicant: Siemens Aktiengesellschaft, Munich (DE)

(72) Inventor: Johannes Georg Korporaal, Forchheim (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 553 days.

(21) Appl. No.: 15/079,477

(22) Filed: Mar. 24, 2016

(65) Prior Publication Data

US 2016/0296178 A1    Oct. 13, 2016

(30) Foreign Application Priority Data

Apr. 7, 2015    (DE) .................. 10 2015 206 155

(51) Int. Cl.
*A61B 6/03*    (2006.01)
*A61B 6/00*    (2006.01)
(Continued)

(52) U.S. Cl.
CPC .............. *A61B 6/032* (2013.01); *A61B 6/481* (2013.01); *A61B 6/5288* (2013.01);
(Continued)

(58) Field of Classification Search
CPC ......... A61B 5/055; A61B 6/032; A61B 6/481; A61B 6/5288; A61B 6/5211;
(Continued)

(56) References Cited

U.S. PATENT DOCUMENTS 6,496,560 B1    12/2002    Lin
6,512,807 B1 *    1/2003    Pohlman ................ A61B 6/481
                                                                         378/19
(Continued)

FOREIGN PATENT DOCUMENTS

CN    101889872 A    11/2010

OTHER PUBLICATIONS

"Dynamic contrast-enhanced imaging techniques: CT and MRI" O'Connor et al., The British Journal of Radiology, 84 (2011), S112-S120.*

(Continued)

*Primary Examiner* — Katherine L Fernandez
*Assistant Examiner* — Yi-Shan Yang
(74) *Attorney, Agent, or Firm* — Harness, Dickey & Pierce, P.L.C.

(57) ABSTRACT

A method is described for determination of an initialization time point of imaging of a region of interest of an object to be examined. A slice of the object is selected for bolus-tracking images in which the flow of a fluid flowing toward the region of interest is observable. A plurality of bolus-tracking images of the slice is taken. Time-density curves are determined based upon intensity values assigned to the individual image points acquired in the plurality of bolus-tracking images for the selected slice. Individual image points are divided into groups according to similarity of time-density curves assigned to the individual image points. Finally, the time at which an intensity value assigned to one of the groups exceeds a threshold value is determined. Also described are a method for carrying out the imaging of a region of interest; an initialization time point determination device; and a computed tomography system.

18 Claims, 6 Drawing Sheets

(51) Int. Cl.
  *G06T 7/00* (2017.01)
  *A61B 5/055* (2006.01)
  *G01R 33/56* (2006.01)

(52) U.S. Cl.
  CPC ............ *G06T 7/0016* (2013.01); *A61B 5/055* (2013.01); *G01R 33/5601* (2013.01); *G06T 2207/10081* (2013.01); *G06T 2207/10088* (2013.01); *G06T 2207/30104* (2013.01)

(58) Field of Classification Search
  CPC ...... G01R 33/5601; G06T 2207/10081; G06T 2207/10088; G06T 2207/30104; G06T 7/0016; G06T 2207/20021; G06T 2207/30101; G06T 7/0012
  See application file for complete search history.

(56) References Cited

U.S. PATENT DOCUMENTS

| | | | | |
|---|---|---|---|---|
| 6,745,066 B1* | 6/2004 | Lin | ........................ | A61B 6/481 600/425 |
| 7,715,519 B2* | 5/2010 | Tsukagoshi | ............ | A61B 6/032 378/4 |
| 2008/0119715 A1* | 5/2008 | Gonzalez Molezzi | ...................... | A61B 6/481 600/407 |
| 2010/0292570 A1 | 11/2010 | Tsukagoshi | | |
| 2011/0046498 A1* | 2/2011 | Klap | .................... | A61B 5/0205 600/534 |
| 2012/0290521 A1* | 11/2012 | Frank | ................... | G06N 99/005 706/45 |
| 2013/0279783 A1* | 10/2013 | Schmitt | .................. | A61B 6/032 382/131 |
| 2013/0322718 A1* | 12/2013 | Kao | .................... | G06T 11/008 382/131 |
| 2016/0078619 A1* | 3/2016 | Hsieh | .................... | A61B 6/032 378/4 |

OTHER PUBLICATIONS

Press, William H. et al.: "Numerical Recipes: The Art of Scientific Computing, 3rd Edition", in: Cambridge University Press, New York, NY, Chapter 16, pp. 840-898, 2007.
Office Action for corresponding Chinese Application No. 201610210525.7 dated Jul. 18, 2018 and partial English translation thereof.
Office Action for corresponding Chinese Application No. 201610210525.7 dated Mar. 19, 2019 and English translation thereof.

* cited by examiner

DETERMINING AN INITIALIZATION TIME POINT OF IMAGING USING A CONTRAST MEDIUM

PRIORITY STATEMENT

The present application hereby claims priority under 35 U.S.C. § 119 to German patent application number DE 102015206155.8 filed Apr. 7, 2015, the entire contents of which are hereby incorporated herein by reference.

FIELD

At least one embodiment of the invention generally relates to a method for automatically determining an initialization time point of imaging of a region of interest of an object to be examined. Furthermore, at least one embodiment of the invention generally relates to a method for carrying out imaging of a region of interest. Moreover, at least one embodiment of the invention generally relates to an initialization time point determination device. Finally, at least one embodiment of the invention generally relates to an imaging medical device.

BACKGROUND

Modern imaging methods are frequently used to generate two- or three-dimensional image data that can be used to visualize an imaged object to be examined and in addition also for further applications.

Imaging methods are frequently based on the acquisition of X-rays, wherein so-called projection measurement data is generated. For example, projection measurement data can be acquired with the aid of a computed tomography system (CT system). In CT systems, typically a combination of an X-ray source and an oppositely arranged X-ray detector arranged on a gantry rotates around a measuring chamber in which the object to be examined (referred to hereinafter without restricting generality as the patient) is located. In this case, the center of rotation (also known as the "isocenter") coincides with a so-called system axis z. During the course of one more revolutions, the patient is irradiated with X-rays from the X-ray source wherein projection measurement data or X-ray projection data is acquired with the aid of the opposite X-ray detector.

The X-ray detectors used for CT imaging typically have a plurality of detection units which in most cases are arranged in the form of a regular pixel array. Each of the detection units generates a detection signal for X-rays incident on the detection units, said detection signal being analyzed with regard to intensity and spectral distribution of the X-rays at specific times in order to obtain conclusions regarding the object to be examined and to generate projection measurement data.

Other imaging techniques are based on magnetic resonance imaging. During the generation of magnetic resonance images, the body to be examined is exposed to a relatively high basic magnetic field of, for example, 1.5 tesla, 3 tesla, or in newer high magnetic field systems, even 7 tesla and more. Then, a suitable antenna device emits a radio-frequency excitation causing the nuclear spins of specific atoms that are excited to resonance by this radio-frequency field in the magnetic field to be flipped by a specific flip angle relative to the magnetic field lines of the basic magnetic field. The radio-frequency signal radiated on the relaxation of the nuclear spins, the so-called magnetic resonance signal, is then detected with suitable antenna devices, which can also be identical to the transmission antenna device. The raw data acquired in such a manner is finally used to reconstruct the desired image data. For spatial encoding, respective defined magnetic field gradients are superimposed on the basic magnetic field during the transmission and readout or reception of the radio-frequency signals.

The imaging methods are not only suitable for the imaging reproduction of anatomical structures. In addition, work is increasingly being performed on functional imaging by means of the above-described imaging methods with which functional or dynamic measured variables can be determined, such as, for example, the measurement of the blood flow rate in blood vessels.

In the visualization of functional relationships and also patients' body structures, so-called contrast media are used in medicinal imaging. However, before contrast-medium-supported medical imaging can be started, it is necessary to ensure that, after the injection of the contrast medium into the patient's body, the contrast medium is also located in the region of interest of the patient's body. One possibility for visualizing the distribution of the contrast medium in the body consists in the performance of a so-called bolus-tracking scan (BT scan in short), which is performed before the actual imaging. A BT scan of this kind can entail a time-dependent CT image with low resolution, with which a time-density curve of a sub-area of a region of interest is acquired. Usually, such a sub-area for a BT scan includes a slice, which is embodied orthogonally to the z-direction, the direction of the system axis of the imaging system, and is also considered. Specifically, with the BT scan, attenuation values are acquired as a function of time and space in a sub-area of the region of interest in which generally an artery is located. If the injected contrast medium now flows through the observed artery, the attenuation values are significantly increased. If a predetermined threshold value for the attenuation values is exceeded, for example 150 Hounsfield Units (HU), this can be interpreted as meaning that the contrast medium is present in the region of interest in a sufficient concentration and the actual examination of the image started. The position and size of the sub-area examined with the BT scan can usually also be amended manually.

However, manual adaptation and localization of the sub-area is only effective if the anatomical structures can be clearly identified on a previously compiled overview image (see FIG. 1). If, however, the decisive structures are very small and difficult to differentiate, such as, for example, in the case of blood-carrying arteries in the neck region, identification solely on the basis of this overview image can be very difficult. In such cases, however, it is nevertheless necessary to define a sub-area for the BT method. The sub-area is then generally located outside the patient so-to-speak "in the air" and the distribution of the contrast medium is instead monitored via corresponding imaging by direct observation of the patient. If the operator has the impression that the contrast medium is present in the region of interest in a sufficient concentration, the actual imaging is started manually.

A procedure of this kind requires the user to have experience and is in addition not particularly precise. Often, the time for starting the imaging is set too late so that the total time for which the contrast medium is located in the patient is extended. However, in principle, it is attempted to achieve the shortest possible dwell time of the contrast medium in the body since the contrast medium can be stressful for the human body. Starting the imaging too early can result in a deterioration of the image quality. In the most unfavorable case, it is even necessary to repeat the imaging and the administration of the contrast medium, which is an additional stress for the patient.

SUMMARY

At least one embodiment of the present invention develops, in connection with contrast medium imaging, a more exact and more effective method for the determination of the initialization time point of the imaging even without direct intervention on the part of the operator.

At least one embodiment is directed to a method for automatically determining an initialization time point of imaging of a region of interest of an object to be examined; at least one embodiment is directed to a method for carrying out imaging of a region of interest; at least one embodiment is directed to an initialization time point determination device; and at least one embodiment is directed to an imaging medical device.

A method, according to at least one embodiment of the invention, is disclosed for automatically determining an initialization time point of imaging of a region of interest of an object to be examined. A slice or a plane lying in the slice of the object to be examined is selected for subsequent bolus-tracking images in which a fluid or the flow of a fluid, including, for example, a contrast medium, to the region of interest can be observed. The plane can, for example, form a cut-set with the region to be depicted. The selection of the slice or the plane in which the bolus tracking subsequently takes place is performed with the aid of a topogram. Then, a plurality of bolus-tracking images of the selected slice is taken. With bolus tracking, intensity values, in the case of a CT scan, attenuation values, of the selected slice are acquired.

Repeating this imaging at subsequent time points produces a time-density curve for each image point in this slice. Hereinafter, the term image point includes both three-dimensional voxels and two-dimensional pixels. Therefore, in this context, an image point xi can be understood to mean a small volume unit or an associated grid point in a three-dimensional grid.

The method according to at least one embodiment of the invention for carrying out imaging of a region of interest uses the method according to at least one embodiment of the invention for automatically determining an initialization time point of imaging of a region of interest of an object to be examined. Imaging is then started at the initialization time point, which was determined with the method according to at least one embodiment of the invention for automatically determining an initialization time point of imaging of a region of interest of an object to be examined or with an additional waiting time 5 to 10 s after the initialization time point. If, therefore, there is no waiting time after the initialization time point, the initialization time point can also be considered to be the starting time point for the imaging.

The imaging medical device according to at least one embodiment of the invention, in particular a computed tomography system, comprises a control device with the initialization time point determination device according to the invention.

The implementation of at least one embodiment of the invention in a CT system has the advantages that the scan duration of a CT system is relatively short. Unlike the case with imaging with MRI systems, which can require several minutes, this lasts a few seconds only. This is particularly advantageous in the case of the examination of emergency patients when any time delay can be life-threatening. Moreover, CT systems are more widely used and more economically efficient than MRI systems.

The essential components of the initialization time point determination device according to at least one embodiment of the invention for determining an initialization time point of imaging of a region to be depicted of an object to be examined can for the main part be embodied in the form of software components. This in particular relates to the reconstruction unit, the analysis unit and the initialization time point determination unit. In principle, however, when particularly fast calculations are concerned, the components can also be partially implemented in the form of software-supported hardware, for example FPGAs or the like. Similarly, for example when only a transfer of data from other software components is involved, the required interfaces can also be embodied as software interfaces. However, they can also be embodied as hardware interfaces actuated by suitable software.

A substantially software-based implementation has the advantage that previously used control devices can also be simply retrofitted by a software update in order to operate in the manner according to at least one embodiment of the invention. Insofar, the object is also achieved by a computer program product or non-transitory computer readable medium, with a computer program which can be loaded directly into a storage device of a control device of an imaging system, preferably a computed tomography system, with program segments in order to carry out all steps of the method according to the invention when the program is executed in the control device. In addition to the computer program, a computer program product can optionally include additional elements such as, for example, documentation and/or additional components, including hardware components, such as, for example, hardware keys (dongles etc.) for using the software.

Transportation to the control device and/or storage on or in the control device be achieved by a computer-readable medium, for example a memory stick, a hard disc or any other transportable or permanently installed data carrier on which the program segments of the computer program that can be read-in and executed by a computing unit of the control device are stored. To this end, the computing unit can, for example, comprise one or more interacting microprocessors or the like.

The dependent claims and the subsequent description all contain particularly advantageous embodiments and developments of the invention. Here, in particular the claims of one claim category can also be developed similarly to the dependent claims of another claim category. Moreover, within the context of the invention, it is also possible to combine the various features of different example embodiments and claims to form new example embodiments.

BRIEF DESCRIPTION OF THE DRAWINGS

The invention is described again in more detail in the following with reference to the attached figures and example embodiments. The figures show.

DETAILED DESCRIPTION OF THE EXAMPLE EMBODIMENTS

Figure 1:
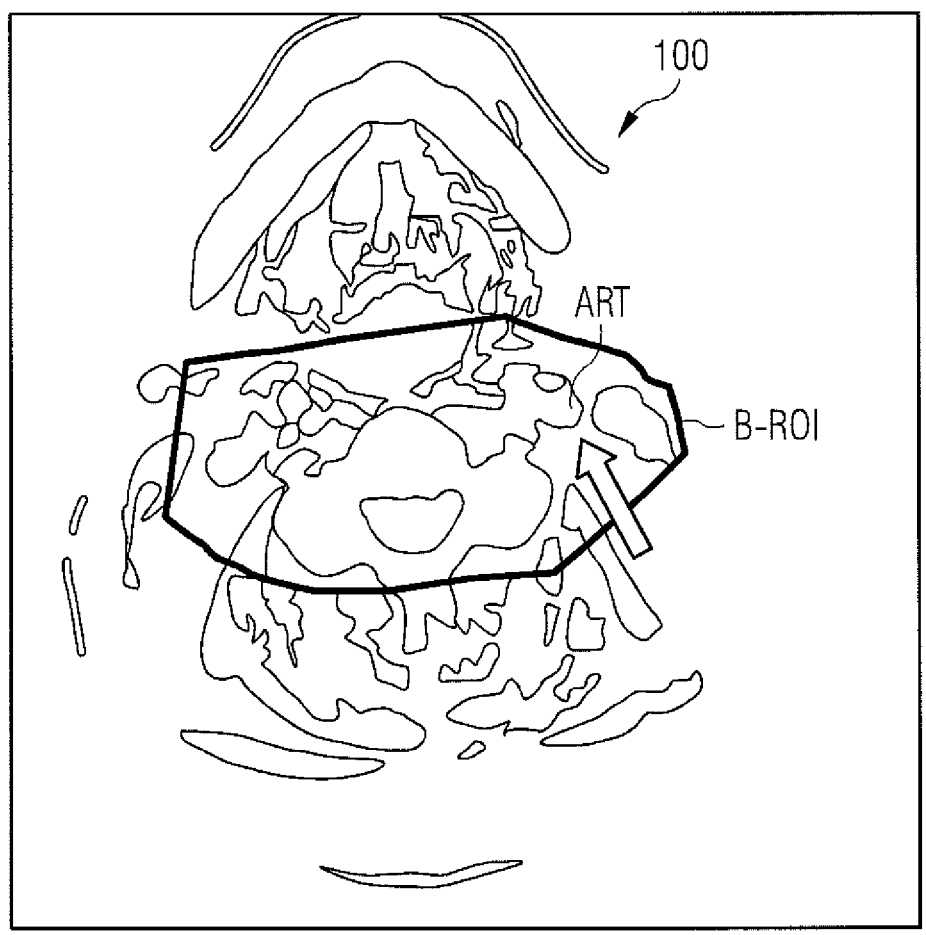
FIG. 1 a depiction of a previously recorded overview image used for the identification and localization of an artery for a bolus-tracking scan, FIG. 2 a flow diagram illustrating a method for performing CT imaging of a region of interest according to a first example embodiment of the invention, FIG. 3 a diagram illustrating the division of measured values von BT images into individual groups or clusters with the method according to the first example embodiment of the invention, FIG. 4 a flow diagram illustrating a method for performing CT imaging of a region of interest according to a second example embodiment of the invention, FIG. 5 a schematic representation of a initialization time point determination device according to an example embodiment of the invention, FIG. 6 a computed tomography system according to an example embodiment of the invention.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Before discussing example embodiments in more detail, it is noted that some example embodiments are described as processes or methods depicted as flowcharts. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Further, although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

A method, according to at least one embodiment of the invention, is disclosed for automatically determining an initialization time point of imaging of a region of interest of an object to be examined. A slice or a plane lying in the slice of the object to be examined is selected for subsequent bolus-tracking images in which a fluid or the flow of a fluid, including, for example, a contrast medium, to the region of interest can be observed. The plane can, for example, form a cut-set with the region to be depicted. The selection of the slice or the plane in which the bolus tracking subsequently takes place is performed with the aid of a topogram. Then, a plurality of bolus-tracking images of the selected slice is taken. With bolus tracking, intensity values, in the case of a CT scan, attenuation values, of the selected slice are acquired.

Repeating this imaging at subsequent time points produces a time-density curve for each image point in this slice. Hereinafter, the term image point includes both three-dimensional voxels and two-dimensional pixels. Therefore, in this context, an image point xi can be understood to mean a small volume unit or an associated grid point in a three-dimensional grid.

Alternatively, an image point can also be a two-dimensional grid point in a slice plane. Hence, the time-density curves are determined for each individual image point on the basis of intensity values, which were assigned to the individual image points in the slice during the plurality of bolus-tracking images of the selected slice.

A time-density curve should be understood to be the temporal course of the intensities of the image points of the selected slice. The individual image points are divided into groups of image points according to the similarity of the time-density curves assigned to the individual image points. In this context, the term group designates a subset of image points out of the total amount of image points, which form the slice acquired during the BT imaging.

In this case, individual image points should be clearly assigned to a group, i.e. the subsets or image points assigned to the groups do not form any cut-sets. The division into groups is performed on the basis of the temporal course of the time-density curves. Therefore, at least two BT scans must be available to enable a division of this kind to be performed. This division is preferably performed with the aid of learning or self-organizing iterative methods. I.e., after each additional BT scan, a new division of the individual image points into groups is performed for example. Finally, the time is determined at which an intensity value assigned to a group reaches, or even exceeds, a predetermined threshold value.

In the case of imaging with a CT system, on the arrival of an iodine-containing contrast medium, it is determined that a threshold value has been exceeded, while, in the case of imaging with MRI systems, for example, it is possible to determine when a specific threshold value is fallen below. Expressed generally, the temporal behavior of the intensity values with respect to the threshold value depends upon the type of imaging and the contrast medium used. The individual groups are assigned a number of image points which are in turn each assigned a time-density curve. The function values of these time-density curves can be used to determine a time-density curve representing the group or even a time-density relationship. In the simplest case, the time-density relationship simply includes all the time-density curves assigned to the group. Alternatively, the time-density relationship can also be determined as an averaged time-density curve from the time-density curves. For example, the mean values calculated thereby can also be weighted mean values.

In the step in which a check is performed to see whether a predetermined threshold value has been exceeded, the functional values of the time-density curve representing the group, which, for example, include intensity values, are now compared with the threshold value. If the threshold value is exceeded, the conclusion is drawn that the initialization time point for the actual imaging has been reached.

The method according to at least one embodiment of the invention for carrying out imaging of a region of interest uses the method according to at least one embodiment of the invention for automatically determining an initialization time point of imaging of a region of interest of an object to be examined. Imaging is then started at the initialization time point, which was determined with the method according to at least one embodiment of the invention for automatically determining an initialization time point of imaging of a region of interest of an object to be examined or with an additional waiting time 5 to 10 s after the initialization time point. If, therefore, there is no waiting time after the initialization time point, the initialization time point can also be considered to be the starting time point for the imaging.

The initialization time point determination device according to at least one embodiment of the invention for determining an initialization time point of imaging of a region to be depicted of an object to be examined comprises an input interface for receiving selection guidelines with respect to the selection of a slice or plane of the object to be examined for subsequent bolus-tracking images, in which a fluid or the flow of a fluid, for example with a contrast medium, to the region of interest can be observed. The initialization time point determination device according to at least one embodiment of the invention furthermore comprises an actuation unit for actuating an imaging unit for taking a plurality of bolus-tracking images of the selected slice. The image recording unit can, for example, be a CT scanner. Moreover, the initialization time point determination device according to at least one embodiment of the invention also comprises a raw data acquisition unit for the acquisition of the raw data acquired during the plurality of bolus-tracking images. The initialization time point determination device according to at least one embodiment of the invention also comprises a reconstruction unit for the reconstruction of image data including intensity values assigned to individual image points on the basis of the raw data acquired.

The initialization time point determination device according to at least one embodiment of the invention further comprises an analysis unit for dividing the individual image points into groups according to the similarity of the time-density curves assigned to the individual image points, which were determined on the basis of the intensity values assigned to the individual image points. The initialization time point determination device according to the invention also includes an initialization time point determination unit for the determination of the time at which an intensity value assigned to one group of the groups reaches, or even exceeds, a predetermined threshold value.

The imaging medical device according to at least one embodiment of the invention, in particular a computed tomography system, comprises a control device with the initialization time point determination device according to at least one embodiment of the invention.

The implementation of at least one embodiment of the invention in a CT system has the advantages that the scan duration of a CT system is relatively short. Unlike the case with imaging with MRI systems, which can require several minutes, this lasts a few seconds only. This is particularly advantageous in the case of the examination of emergency patients when any time delay can be life-threatening. Moreover, CT systems are more widely used and more economically efficient than MRI systems.

The essential components of the initialization time point determination device according to at least one embodiment of the invention for determining an initialization time point of imaging of a region to be depicted of an object to be examined can for the main part be embodied in the form of software components. This in particular relates to the reconstruction unit, the analysis unit and the initialization time point determination unit. In principle, however, when particularly fast calculations are concerned, the components can also be partially implemented in the form of software-supported hardware, for example FPGAs or the like. Similarly, for example when only a transfer of data from other software components is involved, the required interfaces can also be embodied as software interfaces. However, they can also be embodied as hardware interfaces actuated by suitable software.

A substantially software-based implementation has the advantage that previously used control devices can also be simply retrofitted by a software update in order to operate in the manner according to at least one embodiment of the invention. Insofar, the object is also achieved by a computer program product or non-transitory computer readable medium, with a computer program which can be loaded directly into a storage device of a control device of an imaging system, preferably a computed tomography system, with program segments in order to carry out all steps of the method according to the invention when the program is executed in the control device. In addition to the computer program, a computer program product can optionally include additional elements such as, for example, documentation and/or additional components, including hardware components, such as, for example, hardware keys (dongles etc.) for using the software.

Transportation to the control device and/or storage on or in the control device be achieved by a computer-readable medium, for example a memory stick, a hard disc or any other transportable or permanently installed data carrier on which the program segments of the computer program that can be read-in and executed by a computing unit of the control device are stored. To this end, the computing unit can, for example, comprise one or more interacting microprocessors or the like.

The dependent claims and the subsequent description all contain particularly advantageous embodiments and developments of the invention. Here, in particular the claims of one claim category can also be developed similarly to the dependent claims of another claim category. Moreover, within the context of the invention, it is also possible to combine the various features of different example embodiments and claims to form new example embodiments.

In one embodiment of the method according to at least one embodiment of the invention, the patient is given a contrast medium before the first bolus tracking imaging. This can, for example, be performed prior to the start of the method according to the invention by a doctor or an injector. The injection of a contrast medium enables the visualization of functional parameters or specific anatomical structures of a patient.

It is also preferable for at least one of the groups of which the assigned time-density curve(s) is most similar to a reference artery signal curve to be identified as a group with an arterial signal. The specification of modeled cluster centers for example enables a reference artery signal curve to be used directly during the imaging of the groups of image points. However, if the groups are initially formed by initial groups and adapted in a self-organized manner to the data acquired within the framework of an iterative process, following the formation of the groups they can also be used as a comparative curve, which is compared to the time-density curves assigned to the individual groups in order to determine which group is entailed. In other words, the iterative process searches for the best solution so-to-speak automatically.

Particularly preferably, with the method according to the invention, the actual imaging of the patient includes CT imaging and in this case the intensity values include attenuation values obtained during the imaging by the reconstruction of the raw data acquired.

Alternatively, the imaging with the method according to at least one embodiment of the invention can also include MRI imaging.

The method according to at least one embodiment of the invention can be carried out particularly effectively when a clustering method is used for the division of the image points into groups.

A cluster method is a method with which parameters to be grouped are arranged around cluster centers such that the sum of the squares of the distances between the parameters to be group and the cluster centers is minimal. With so-called K-means clustering, the cluster centers are initialized at the start and changed during the method such that, with each iteration step, new cluster centers are calculated as the average value of the grouped parameters contained in the respective group and subsequently the grouping of the parameters around the newly calculated cluster centers is performed according to the criterion of the smallest sum of the squares of the distances between the parameters and the newly calculated cluster centers.

One method of this kind suitable for use with the method according to the invention is K-means clustering. Alternatively, it is also possible to use so-called hierarchical clustering with which cluster centers are predefined in the form of models.

Cluster methods of this kind are inter alia published in PRESS, WILLIAM H. ET AL.: "Numerical Recipes: The Art of Scientific Computing, 3rd Edition", in: Cambridge University Press, New York, N.Y., Chapter 16, 2007, pp. 840-898.

In one variant of the method according to at least one embodiment of the invention for automatically determining an initialization time point of imaging of a region of interest of an object to be examined, a group of image points with which the intensity values first exceed a threshold value is identified as a group with an arterial signal. A first increase in the intensity values is interpreted as meaning that the contrast medium is starting to flow through an artery through the selected slice. In this case, advantageously a group can also include a plurality of arteries which are reached by the contrast medium at approximately the same time.

In order to suppress interference signals during the determination of the initialization time point, preferably groups with time-density curves which are correlated with the heart rate or the respiration of the patient are identified as separate groups. These groups are used to eliminate predictable periodic interference due to body movements during the process of division into groups.

In a particularly preferred variant of the method according to at least one embodiment of the invention, the number of groups is established in advance in dependence on the maximum time to be required for the determination method. If the determination method only takes a short time, the number of groups is reduced. However, this also reduces the accuracy of the determination of the initialization time point.

It is also advantageous for the bolus-tracking images to be taken in a restricted sub-area of interest of the selected slice which is defined as the region in which an arterial signal is to be expected. In this case, it is possible to reduce the recording time and, due to the lower number of image points in the BT images, the grouping of the individual image points takes place more quickly and the initialization time point can be determined with less computing effort. The definition of the restricted sub-area can, for example, be performed with reference to a previously compiled overview image of the slice to be depicted in the BT scans.

The method according to at least one embodiment of the invention can also be sped up if group centers are defined from models in advance for the individual groups in that each of the groups is assigned a predetermined time-density curve as a group center. If the time-density curves assigned to the group centers, wherein said time-density curves can, for example, be known from empirical values, correspond extremely precisely to the time-density curves assigned to the image points to be grouped, the grouping and the determination of the initialization time point can be significantly sped up. However, a flexible iterative adaptation process for the group centers requiring time or computing capacity is not used with this time-saving variant.

Alternatively, during the grouping, the initial group centers selected can be randomly chosen group centers, which during the use of the cluster method, which is also called a clustering method, can be adapted to the time-density curves assigned to the image points grouped therearound. The adaptation of the group centers or cluster centers can be achieved by the formation of a mean value of the time-density curves for the image points assigned to a group or a cluster and setting the mean value as a new group center. This enables the group division to be adapted flexibly to individual measured data sets. In an alternative variant of this special type of clustering, the initial group centers are predetermined from models, for example in that starting values are prespecified on the basis of empirical values and subsequently adapted iteratively to the measured data acquired by means of the described adaptation process.

Unlike the case with the variant with which the individual group centers are predefined from models and fixed, in the case of the randomly chosen specification of initial group centers, it is not at first known which group is assigned to the arterial signal sought. This assignment can, for example, be determined following the division of the groups by comparison with a reference signal or a reference time-density curve.

A further simplification and acceleration of the method according to at least one embodiment of the invention can be achieved if, during the step of the division into groups of image points, the only image points taken into account are those with assigned intensity values whose intensity values are within a predetermined value interval. In this case, the value interval for the case of imaging with the aid of a CT system preferably includes a range of from −50 HU to 150 HU in order, for example, to exclude bone and lung tissue.

In order to compensate body movements with the method according to at least one embodiment of the invention, it is possible for sets of image data recorded with the bolus-tracking images to be recorded successively. The correction of the image data acquired enabled by the registration produces a correct spatial assignment of the intensity values acquired during the imaging.

In one variant of the method according to at least one embodiment of the invention, a hierarchical cluster method or alternatively a K-means cluster method can be used as a cluster method.

FIG. 1 is a depiction of a head-and-neck region 100, which is conventionally generated prior to the actual CT imaging and prior to the BT scan during a premonitoring process in order to enable a sub-area of interest B-ROI to be defined in which a BT scan is to be performed for determining a fluid or a contrast-medium concentration. The depiction corresponds to a plane BT-S, for which is expected that it will be possible to observe therein the flow of the fluid or the contrast medium to the region of interest during the course of the method. In the case shown in FIG. 1, the arteries ART sought can hardly be identified so that, with the conventional method, the correct region B-ROI for the BT scan can only be localized with difficulty.

Figure 2:
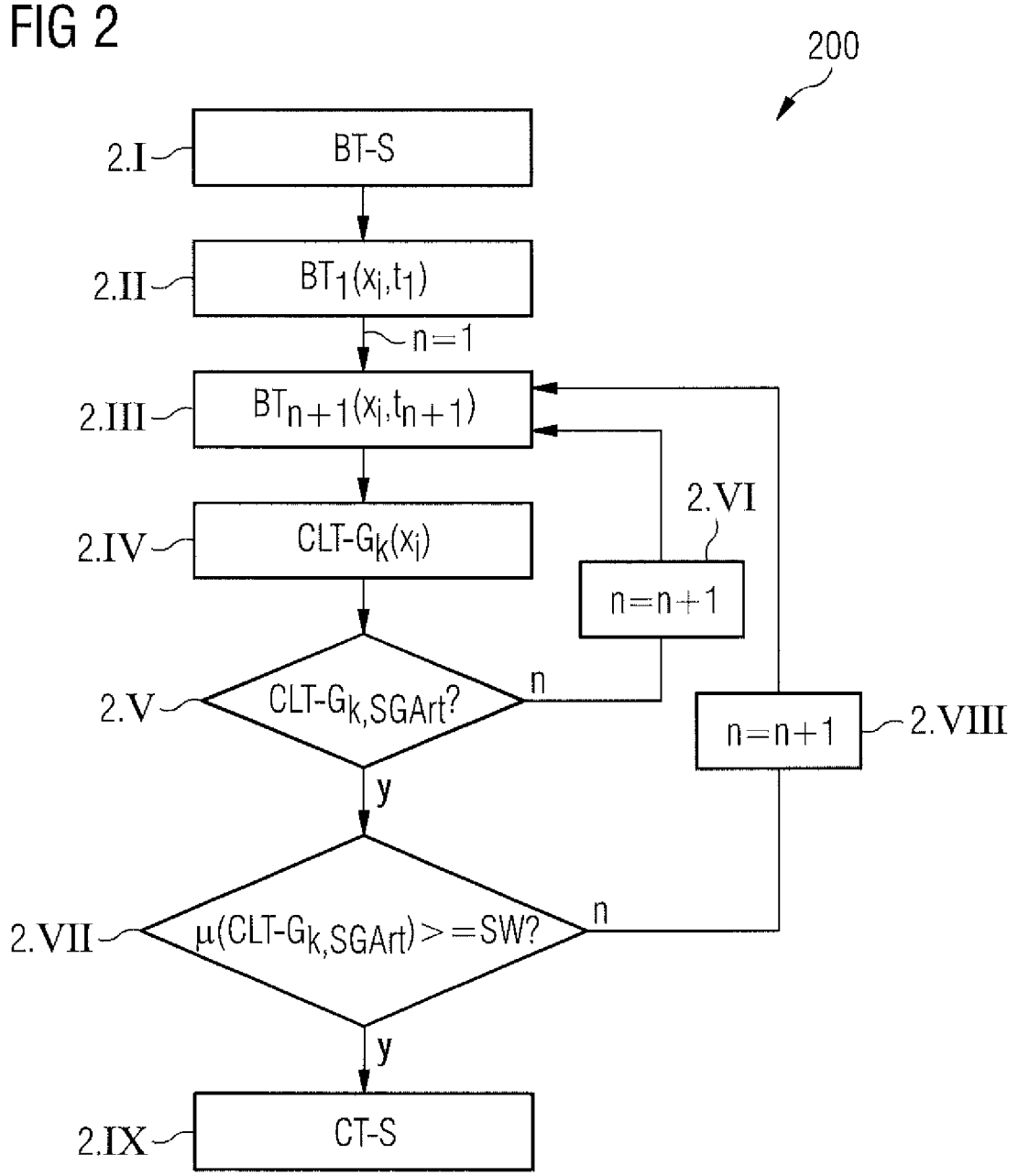

FIG. 2 illustrates an example embodiment of the Method 200 for the automatic determination of the initialization time point of a CT image CT-S in a flow diagram. In Step 2.I, initially a plane BT-S is determined for example with the aid of a topogram in which a BT scan BT is to be performed. Although a CT image is divided in the z-direction into a plurality of slices, with BT images, usually one slice or a plane included therein, in which the flow of a contrast medium to the region of interest can be observed, is sufficient. This enables the exposure to radiation during the BT scan to be restricted to the selected slice.

Following the determination of a suitable slice BT-S for the BT images BT, a first BT scan BT1(xi,t1) is performed in Step 2.II. For this image, the patient to be examined has been given a contrast medium in advance, i.e. prior to the start of the Method 200. During the first BT scan BT1(xi,t1), imaging is performed of image points xi of the selected slice BT-S at a first time t1 with which attenuation values $\mu(xi,t1)$ in the selected slice are acquired in this example embodiment.

In Step 2.III, a second BT scan BT2(xi,t2) is recorded at the time t2 (with a starting value 1 for a running variable n, on the first pass of Step 2.III, the variable index n+1 of the BT scan BTn+1 has the specific index value 2) from the selected slice BT-S. With the Method 200, at least one second image recording is required in order subsequently to divide individual image points xi into groups as a function of the course of a time-density curve for each image point xi of the slice BT-S. During the division into the individual groups, it is not the absolute level of the attenuation values $\mu$ that is primarily taken into consideration, but the value changes $\Delta\mu$ as a function of the time t. In this case, if reference is made to the density, it is assumed that the density correlates with the measured attenuation values $\mu(xi,tn)$, which is usually stated in Hounsfield units HU. The individual BT scans are usually acquired in time intervals of from 1 to 2 seconds.

In Step 2.IV, grouping of the image points xi is performed with respect to a same or similar time-density response. I.e., the BT scans BTn acquired up to this time are evaluated and conclusions drawn therefrom regarding the association of the image points xi with individual functional groups. This procedure is based on the fact that, in regions reached by the fluid, for example a contrast medium or a fluid containing a contrast medium, the attenuation values rise. Moreover, the time or temporal sequence in which the attenuation values rise to a specific point can be used to draw conclusions as to whether this entails an artery or a vein. Division into groups CLT-Gk is performed on the basis of so-called clustering. During the clustering, image points xi are grouped with which the temporal response of the curve for the attenuation values takes a similar course. This grouping requires at least two BT scans. With this first example embodiment, the criteria for the division of the groups are not fixed but are produced so-to-speak in a self-organized way on the basis of the acquired measured values. This means that, for example, initial values are specified for group centers and the group centers are adapted to the newly acquired measured data during the method.

In Step 2.V, subsequently the group CLT-Gk,SGArt whose assigned image points or attenuation values have a temporal response corresponding to the response of an artery exposed to a fluid, for example a contrast medium, is selected from the groups CLT-Gk. For example, a sudden severe increase in the curve for the attenuation values $\mu(xi,tn)$ or the time-density curve is interpreted as an artery signal SGArt. A strong increase can be used as a differentiation criterion since an increase of the attenuation values in the veins is normally much weaker and hence can be clearly distinguished from the strong increase in an artery. In addition, the increase in the veins starts later so that, in principle, the arteries are always the first to signal the flow of the contrast medium and the veins only do so later. If, in Step 2.V, none of the image-point groups CLT-Gk display a signal SGArt identifying an artery, identified by "n" in FIG. 2, in this step, the running variable n is incremented by the value 1 followed by a return to Step 2.III. In Step 2.III, a new BT scan BTn+1(Xi,tn+1) is continued, in this case with the value 2 for the running index n. Subsequently, in Step 2.IV, a new grouping of the image points is performed on the basis of the previous BT scans. Subsequently, in Step 2.V, a further check is performed to see whether a signal SGArt identifying an artery is found a group CLT-Gk,SGArt of the defined groups CLT-Gk. If this is the case, as identified with "y" in FIG. 2, in Step 2.VII, this group CLT-Gk,SGArt is checked to see whether an attenuation value $\mu$ assigned to this group CLT-Gk,SGArt exceeds a predetermined threshold value SW. In this case, the attenuation value $\mu$ can, for example, be a current average value, which is assigned to the image points of the selected group CLT-Gk,SGArt or also a single maximum value, which was measured on one of the BT scans for one of the image points of the selected group CLT-Gk,SGArt. If it is determined in Step 2.VII that the threshold value SW was not exceeded, the running variable n is incremented by the value 1 in Step 2.VIII followed by a return to Step 2.III where a new BT scan BTn+1 is performed (with n=3). Subsequently, Steps 2.IV to 2.VII are repeated. If it is determined in Step 2.VII that the threshold value SW is now exceeded, this will be interpreted as a sign that the contrast medium has arrived in the region of interest ROI and the actual imaging CT-S is started in Step 2.IX.

Figure 3:
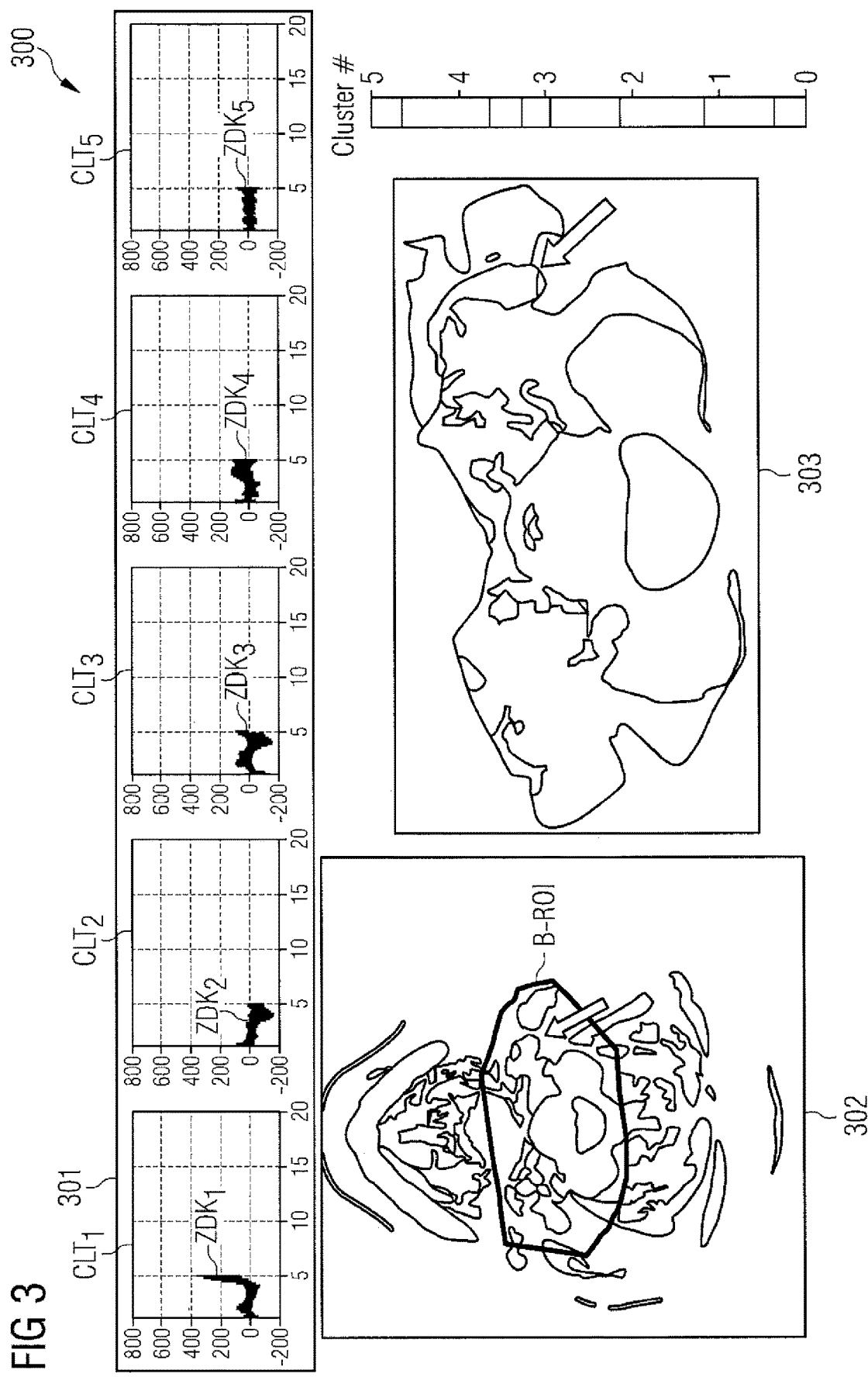

FIG. 3 shows a diagram 300, which divided into three partial diagrams 301, 302, 303. The first or upper partial diagram 301 shows time-density curves ZDK1, . . . , ZDK5, which are assigned to individual groups CLT1, . . . , CLT5. The time-density curves approximately correspond to the stage of the Method 200 in which three BT scans have already been performed after about 5 s. As can be identified with reference to the first partial diagram 301, the time-density curve for the first group CLT1 identifies a strong increase pointing to the conclusion that the image points assigned to this group are image points assigned to an artery. In correspondence with Step 2.V of the method 200, it is, therefore, possible to conclude that the first group CLT1 is the group to be selected in this stage. Moreover, the time-density curve ZDK1 assigned to the first group CLT1 exceeds a typical threshold value of 200 HU, which corresponds to Step 2.VII of the Method 200 wherein it is detected that threshold value has been exceeded. A time-density curve assigned to the respective group CLT1, . . . , CLT5 can, for example, be an averaged curve, which is determined by averaging the time-density curves assigned to the individual image points xi of the respective group CLTi.

The second partial diagram 302 once again depicts the slice view of the head-and-neck region shown in FIG. 1. A sub-area of interest B-ROI of the slice view is marked with a border line. This region is selected in advance since it is expected that the artery whose response will be used to determine an initialization time point for CT imaging with the method according to the invention 200 will be located there. The white arrow positioned in the second partial diagram 302 indicates the position at which the image points of the group CLT1 identified in Step 2.V of the method are located. This position also contains one of the arteries of the patient examined through which the contrast medium is flowing.

However, advantageously according to at least one embodiment of the invention, it is not actually necessary to determine the precise position of the artery since the BT scans are carried out slice-by-slice and the exceeding of the threshold value is determined independently of the determination of the position of the artery. For example, it can also be the case that image points from a plurality of arteries are assigned to the group CLT1, but there is no need to analyze which image points are assigned to which artery with the method according to the invention. One special feature with the example shown in FIG. 3 consists in the fact that, with this patient, only one of the two (left+right) carotid arteries is patent. With the conventional method, it would be possible unfortunately and unwittingly to set the region to be depicted ROI in the wrong, occluded, artery and hence never to obtain a start signal or initial signal for starting the imaging.

The third partial diagram 303 shows different regions with different grey steps of the restricted region B-ROI, wherein, as can be recognized from the scale on the right in the third partial diagram 303, the different grey steps are assigned to different groups, also known as clusters CL. The position, indicated by a white arrow in the third partial diagram 303 is the position at which the image points of the group CLT1 identified in Step 2.V of the method are located. This position also contains one of the arteries of the patient under examination through which the contrast medium flows.

Figure 4:
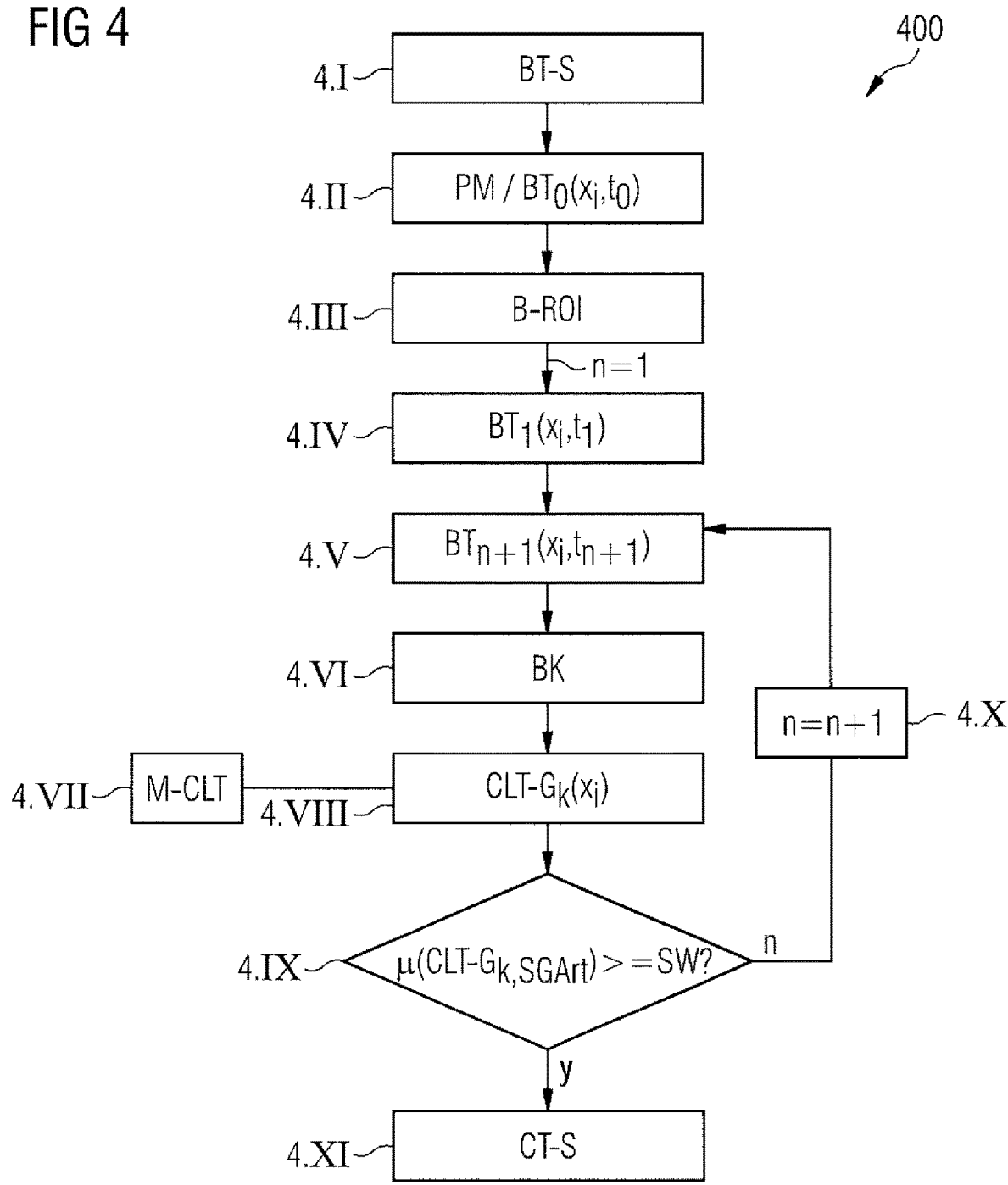

FIG. 4 illustrates a second example embodiment of the Method 400 for the automatic determination of the initialization time point of a CT image CT-S in a flow diagram. In Step 4.I, initially a slice BT-S is determined in which a BT scan BT is to be performed. As already mentioned, a CT image is divided into a plurality of slices in the z-direction. For the BT scan, a slice or a plane BT-S is now selected in which a flow of a contrast medium to the region of interest can be observed. This enables the radiation exposure during the BT scan to be restricted to the selected slice. In addition, with the Method 400, so-called premonitoring PM is additionally performed in Step 4.II. To this end, an overview image is taken of the selected slice BT-S with lower resolution. A PM scan, also designated BT0(xi,t0) in FIG. 4, is therefore identical to a BT scan, apart from the fact that, due to the early time, with premonitoring, it is possible to be certain that no contrast medium is depicted. In order to ensure that the visual impression of the PM scans is the same as the visual impression of BT scans, in principle the same scan parameters are used for both types of imaging.

This overview image is used to draw conclusions regarding the coarse structures in the selected slice and subsequently to define in Step 4.III a restricted region B-ROI in which the artery signal is expected. In this way, it is possible to restrict the number of image points xi acquired with the BT scans in the further course of the Method 400. This enables the Method 400 to be sped up and computing capacity to be saved during the grouping processes and evaluations of the attenuation values acquired.

Following the determination of a suitable slice BT-S for the BT scan BT and of a restricted region B-ROI, a first BT scan BT1(xi,t1) is performed in Step 4.IV. To this end, prior to the start of the Method 400, the patient to be examined is, for example, given a contrast medium. In Step 4.IV, imaging is performed at a first time t1 at which, in this example embodiment, attenuation values $\mu(xi,t1)$ are to be acquired in the selected restricted region B-ROI of the selected slice BT-S.

In Step 4.V, a second BT scan BT2(xi,t2) is recorded at the time t2 (with a starting value 1 of a running variable n, the variable index n+1 of the BT scans BTn+1 has the specific index value 2 during the first pass of Step 4.V) of the restricted region B-ROI of the selected slice BT-S. With the method, at least one second imaging is required in order later to divide individual image points xi into groups as a function of the course of a time-density curve ZDKi for each image point xi of the restricted region B-ROI of the selected slice BT-S. During the division into the individual groups, the absolute level of the attenuation values is not taken in account in the first instance, instead the value changes $\Delta\mu$ are taken into account as a function of the time t. If such a case relates to density, it is assumed that the density correlates with the measured attenuation values $\mu(xi,tn)$, which are usually expressed in Hounsfield units HU. The individual BT scans are usually acquired in time intervals of 1 to 2 seconds.

In Step 4.VI, a so-called baseline correction BK of the acquired time-density curve is performed. The baseline should be understood to be the attenuation values of the individual image points xi measured without the presence of the contrast medium in the selected slice BT-S. These baseline values are subtracted from the attenuation values measured during the BT scans so that the attenuation values standardized in this way only reflect the dynamic response in the selected region B-ROI due to the contrast medium.

Now, in Step 4.VII, unlike the case with the Method 200, according to a first example embodiment of the invention, specific time-density-curve models are specified according to which the image points xi acquired during the BT scans or the intensity values $\mu(xi,tn)$ associated therewith are assigned to the individual groups CLT-Gk. A specification of this kind speeds up the grouping and simplifies the determination of the initialization time point albeit with slightly lower flexibility and adaptability to "atypical" time-density curves, which can possibly result from the measured values of the BT scans. The shape of the model curves can be a function of the index n, i.e. the model curves change with an increasing number of BT images (they become longer), so that the acquired time-density curves can be matched to the correspondingly changed model curves.

In Step 4.VIII, grouping of the image points xi is performed with respect to a same or similar time-density response. I.e., the acquired BT scans BTn acquired up to this time are evaluated and conclusions drawn therefrom regarding the association of the image points xi with individual functional groups. This procedure is based on the fact that, in regions reached by the contrast medium, the attenuation values rise or fall. Moreover, the time or temporal sequence in which the attenuation values rise or fall to a specific point can be used to decide whether this entails an artery or a vein. In the case of a CT scan with an iodine-containing contrast medium, the values rise. However, with MRI acquisition, it can be the case that the MRI signal falls due to the contrast medium.

Division into groups CLT-Gk is performed on the basis of so-called clustering. During the clustering, image points xi are grouped with which the temporal response of the curve for the attenuation values, which corresponds to the time-density curve of the contrast medium, takes a course which in this example embodiment is similar to the model curves specified in Step 4.VII.

These model curves can, for example, be curves with an arterial signal, curves with a vein signal and curves without any contrast-medium signal. Since the group properties or the group centers M-CLT in this example embodiment are fixed, in this case the step (in FIG. 2, Step 2.VI) of the determination of the "correct" group CLT-Gk,SGArt i.e. the group associated with an arterial signal SGArt, is dispensed with since the "correct" group is already known in advance on the basis of the model.

In Step 4.IX, this group CLT-Gk,SGArt is checked to see whether an attenuation value μ assigned to this group CLT-Gk,SGArt exceeds a predetermined threshold value SW. In this case, the attenuation value μ can, for example, be a current average value, which is assigned to the image points of the selected group CLT-Gk,SGArt or also a single maximum value, which was measured on one of the BT scans for one of the image points of the selected group CLT-Gk,SGArt. If it is determined in Step 4.IX that the threshold value SW was not exceeded, the running variable n is incremented by the value 1 in Step 4.X and followed by a return to Step 4.V in which a new BT scan BTn+1 is acquired (with n=2). Subsequently, Steps 4.VI to 4.IX are repeated. If it is determined in Step 4.IX that the threshold value SW is now exceeded, this will be interpreted as a sign that the contrast medium administered to the patient prior to the start of the Method 400 has arrived in the region of interest ROI and the actual imaging CT-S is started in Step 4.XI.

Figure 5:
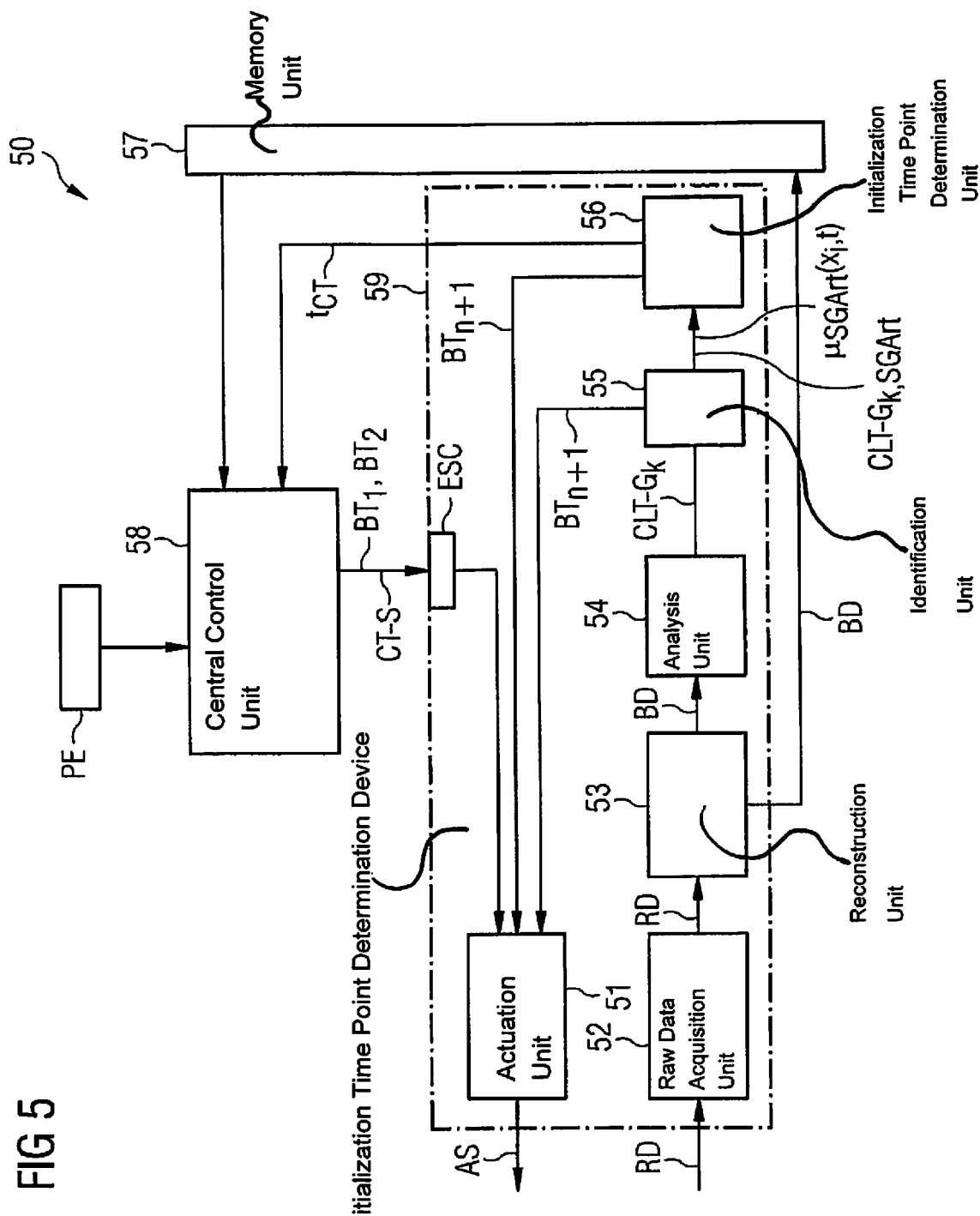

FIG. 5 shows a control device 50 of a CT-system comprising an initialization time point determination device 59 (surrounded by dashed lines) according to an example embodiment of the invention. The control device 50 comprises a control unit 58, which issues control commands and also processes feedback messages from other units of the control device 50 and inputs from peripheral units PE. The control unit 58 issues, for example via an input interface ESC of the initialization time point determination device 59, the command to a control unit 51 of the initialization time point determination device 59, to actuate a CT system (see FIG. 6) with aid of acquisition control signals AS with which imaging is performed. The imaging can, for example, also be an overview image in the form of a topogram to determine a slice or plane BT-S to be selected for subsequent bolus-tracking images. Moreover, the imaging can also be imaging related to the bolus tracking scans BT explained in connection with FIGS. 2 and 4. The imaging can also be the actual contrast-medium-associated imaging CT-S of a region of interest ROI of a patient. Moreover, the control device 50 also comprises a memory unit 57, in which, for example, image data, protocol data or program data for the central control unit 58 are stored.

The arrangement 50 shown in FIG. 5 also comprises a raw data acquisition unit 52 for the acquisition of raw data RD acquired during the aforementioned image recording and a reconstruction unit 53 for the reconstruction of image data BD on the basis of the raw data RD acquired by the raw data acquisition unit 52. For example, the aforementioned BT images BTn are used to determine attenuation values μ of individual image points xi from which the image data BD is compiled.

Moreover, the initialization time point determination device 59 comprises an analysis unit 54 for dividing the individual image points xi into groups CLT-Gk according to a similar temporal response of the intensity values μ(xi,t) assigned to the individual image points xi. As explained in connection with the example embodiments shown in FIGS. 2 and 4, the temporal response of the intensity values μ(xi,t) for the individual groups or group centers assigned to the individual groups or group centers can be determined either in a type of learning process in a self-organized way or from models. Moreover, the initialization time point determination device 59 optionally comprises an identification unit 55. The identification unit 55 is used to identify one of the groups CLT-Gk as a function of the temporal response determined for the intensity values μ(xi,t) assigned to the image points xi of the groups CLT-Gk assigned as a group CLT-Gk,Art with an arterial signal. The identification unit 55 is necessary if the individual group centers are not fixed but are only adapted iteratively during the use of clustering. If, on the other hand, the properties of the individual groups and hence also the group CLT-Gk,SGArt or the group center thereof with an arterial signal are fixed in advance, it is also possible to dispense with the identification unit 55. If it is still not possible to identify the group CLT-Gk,SGArt with an arterial signal, so the identification unit 55 instructs the actuation unit 51 to take an additional BT image BTn+1.

Following the identification of the group CLT-Gk,SGArt with an arterial signal, this information and the intensity data μSGArt(xi,t) assigned to group CLT-Gk,SGArt with an arterial signal are transmitted to an initialization time point determination unit 56, which is configured to determine the time tCT, at which an intensity value μSGArt(xi,t) assigned to group CLT-Gk,SGArt with an arterial signal exceeds a predetermined threshold value SW. The initialization time point determination unit 56 is further configured, for cases in which it is determined that no threshold value SW is exceeded, to instruct the actuation unit 51 that an additional BT image BTn+1 should be performed. Following the determination of the initialization time point tCT, the initialization time point determination unit 56 transmits the initialization time point tCT to the central control unit 58, which starts the actual CT image CT-S at the determined initialization time point tCT with the aid of a corresponding instruction CT-S to the actuation unit 51. Image data BD from the actual imaging CT-S is stored in the memory unit 57.

Figure 6:
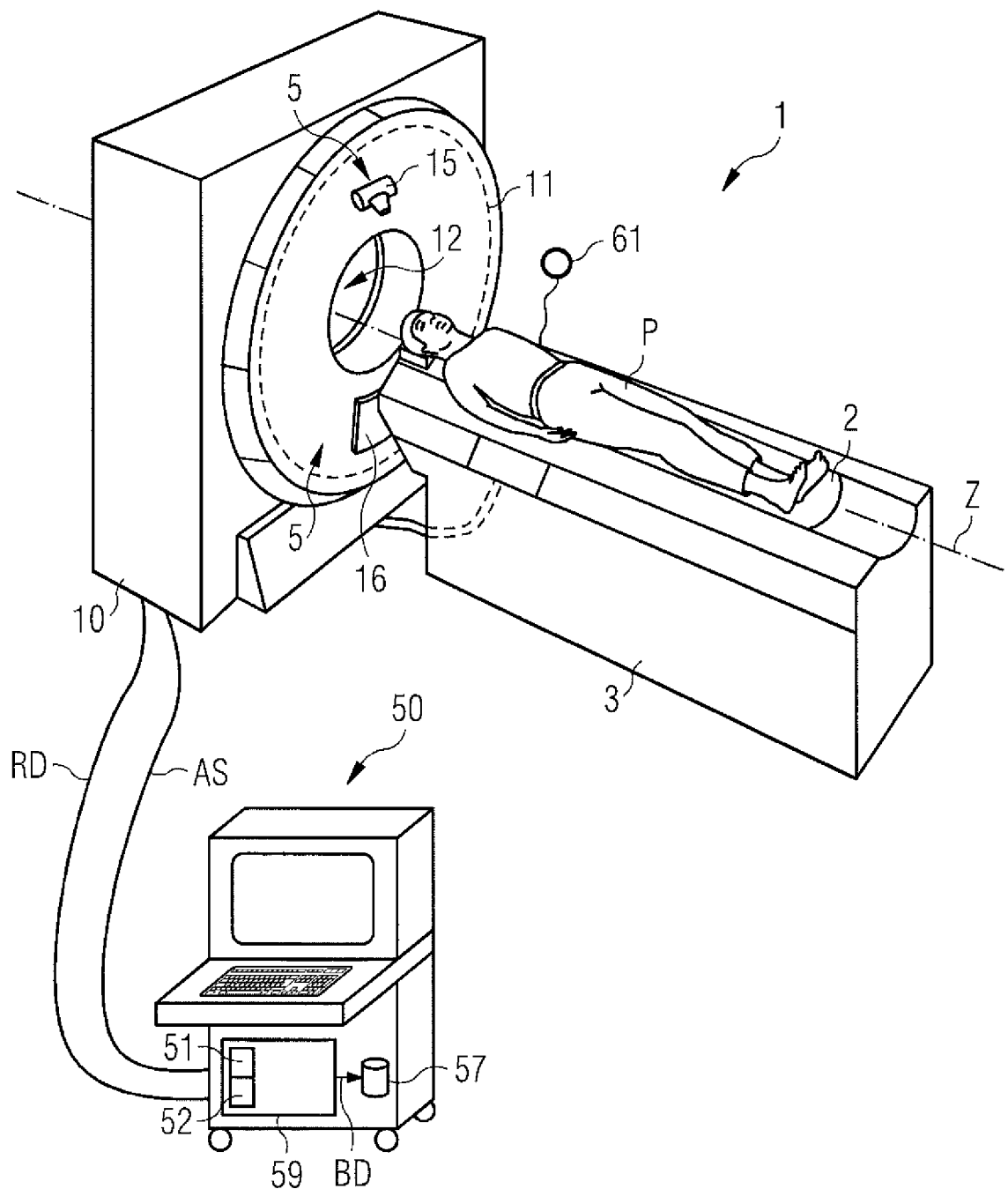

FIG. 6 shows a computed tomography system 1 according to an example embodiment of the invention, which also comprises an initialization time point determination device 59 corresponding to that in FIG. 5 according to an example embodiment. Here, the CT system 1 substantially comprises a conventional scanner 10 in which a projection data acquisition unit 5 with a detector 16 and an X-ray source 15 arranged opposite to the detector 16 on a gantry 11 rotates around a measuring chamber 12. In front of the scanner 10, there is a patient support device 3 or a patient table 3, the upper part 2 of which with a patient P positioned thereupon can be pushed toward the scanner 10 in order to move the patient P through the measuring chamber 12 relative to the detector system 16. The scanner 10 and the patient table 3 are actuated by a control device 50 (see also FIG. 5), which emits acquisition control signals AS via a conventional control interface 51 in order to actuate the entire system according to a prespecified measuring protocol in the conventional manner. In the case of a spiral acquisition, a movement of the patient P along the z-direction corresponding to the system axis z running lengthwise through the measuring chamber 12 and the simultaneous rotation of the X-ray source 15 for the X-ray source 15 relative to the patient P during the measurement produces a helical path. At the same time, the detector 16 always rotates in parallel with the X-ray source 15 in order to acquire projection measurement data RD which is then used for the reconstruction of volume and/or slice-image data. Similarly, it is also possible to carry out a sequential measuring method, for example for the recording of an individual slice, as is the case with the BT scans BTn in the methods according to the invention 200, 400, with which a fixed position in the z-direction is approached and then, during a cycle, a part-cycle or a plurality of cycles the required projection measurement data RD is acquired at the relevant z-position in order to reconstruct a sectional view at this z-position or to reconstruct image data BD from the projection data of a plurality of z-positions. The methods according to the invention 200, 400 can, in principle, also be used with other CT systems, for example with a plurality of X-ray sources and/or detectors and/or with a detector forming a complete ring.

The projection measurement data RD (hereinafter also called raw data RD) acquired by the detector 16 is transmitted via a raw data interface 52, also called a raw data acquisition unit, to the control device 50. This raw data RD is, optionally following suitable preprocessing (for example filtering and/or beam hardening correction), further processed in an image reconstruction unit (see FIG. 5), which in this example embodiment is implemented in the control device 50 in the form of software on a processor. This image reconstruction device uses the raw data RD to reconstruct image data BD with the aid of a reconstruction method. A suitable reconstruction method can, for example, be a reconstruction method based on filtered back-projection.

In cases when the reconstructed image data is image data from an overview image or in particular from a BT scan, this image data BD is subsequently further processed within the control device 50 with the aid of the initialization time point determination device 59, as explained in detail in relation to FIG. 5, and an initialization time point tCT determined. Subsequently, the control device 50 starts the actual imaging CT-S at a determined initialization time point tCT using corresponding acquisition control signals AS.

The image data BD acquired is filed in a memory 57 of the control device 50 and/or is output in the conventional way on the screen of the control device 50. It can also be fed via an interface, which is not shown in FIG. 6, into a network connected to the computed tomography system 1, for example a radiological information system (RIS), and stored in a mass memory accessible there or output on printers or filming stations connected there as images. Hence, the data can be further processed as desired and then stored or output.

In addition, FIG. 6 also shows a contrast medium injection device 61 with which the patient P can be injected with a contrast medium prior to the start of an examination, the behavior of which contrast medium, for example in a vessel or vascular system, can be acquired graphically with the aid of the computed tomography system 1.

Finally, reference is made once again to the fact that, with the above-described Methods 200, 400, the described initialization time point determination device 59 and the described computed tomography system 1 are only preferred example embodiments of the invention and that the invention can be varied by the person skilled in the art without departing from the scope of the invention as disclosed in the claims. For example, the imaging system used can also be a magnetic resonance imaging system. For purposes of completeness, reference is also made to the fact that the use of the indefinite article "a" or "an" does not preclude the possibility that the features in question may also be present on a multiple basis. Similarly, the term "unit" does not preclude the possibility that the unit comprises a plurality of components, which could also be spatially distributed.

The aforementioned description is merely illustrative in nature and is in no way intended to limit the disclosure, its application, or uses. The broad teachings of the disclosure can be implemented in a variety of forms.

Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods. Further, elements and/or features of different example embodiments may be combined with each other and/or substituted for each other within the scope of this disclosure and appended claims.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Further, at least one embodiment of the invention relates to a non-transitory computer-readable storage medium comprising electronically readable control information stored thereon, configured in such that when the storage medium is used in a controller of a magnetic resonance device, at least one embodiment of the method is carried out.

Even further, any of the aforementioned methods may be embodied in the form of a program. The program may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

None of the elements recited in the claims are intended to be a means-plus-function element within the meaning of 35

U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for imaging of a region of interest of an object to be examined, the method comprising:
    selecting a slice of the object to be examined for a plurality of bolus-tracking images, in which a fluid flowing to the region of interest is observable;
    taking the plurality of bolus-tracking images of the selected slice over time;
    determining respective time-density curves based on intensity values assigned to respective individual image points, the respective individual image points being acquired during the taking of the plurality of bolus-tracking images of the selected slice;
    dividing the respective individual image points into a plurality of groups of image points according to a similarity of the respective time-density curves;
    selecting a first group of image points, for which at least one of the intensity values assigned to the first group of image points is first in time to exceed a threshold intensity value among the intensity values assigned to the respective individual image points, as a reference group of image points from among the plurality of groups of image points;
    determining a time, at which the at least one of the intensity values assigned to the reference group of image points exceeds the threshold intensity value, as an initialization time point of the imaging of the region of interest of the object to be examined; and
    controlling an image recording device to start the imaging of the region of interest of the object to be examined based on the initialization time point.

2. The method of claim 1, wherein the method comprises at least one of:
    administering a contrast medium to the object to be examined before taking a first bolus-tracking image of the plurality of bolus-tracking images, and
    identifying at least one of the plurality of groups of image points, for which the respective time-density curves is most similar to a reference artery signal curve, as a group with an arterial signal.

3. The method of claim 1, wherein the imaging includes CT imaging and the intensity values include attenuation values.

4. The method of claim 1, wherein the imaging includes MRI imaging.

5. The method of claim 1, wherein the dividing of the respective individual image points into the plurality of groups of image points is performed based on a clustering method.

6. The method of claim 5, wherein at least one of:
    a number of the plurality of groups of image points into which the respective individual image points are to be divided is defined as a function of a maximum amount of time allowed for the determining of the initialization time point, such that the number of the plurality of groups of image points increases or decreases as the maximum amount of time allowed for the determining increases or decreases,
    the plurality of bolus-tracking images are taken in a restricted partial region of interest of the selected slice, the restricted partial region of interest is a region in which an arterial signal is to be expected,
    group centers are defined in advance from models for the plurality of groups of image points in that a predetermined time-density curve is assigned to each of the plurality of groups of image points as a group center, and
    randomly chosen group centers are selected as initial group centers, adapted during application of the clustering method to the respective time-density curves assigned to the respective individual image points grouped around the initial group centers.

7. The method of claim 5, wherein the clustering method is a hierarchical cluster method or a K-means cluster method.

8. The method of claim 5, wherein, during the dividing of the respective individual image points into the plurality of groups of image points, only image points with the assigned intensity values in a value interval are taken into account.

9. The method of claim 8, wherein at least one of:
    the value interval include a range from −50 HU to 150 HU, and
    images recorded in the plurality of bolus-tracking images are registered in sequence.

10. The method of claim 1, wherein the first group of image points is identified as a group with an arterial signal.

11. The method of claim 1, wherein the groups of image points with the respective time-density curves, which are correlated with a heart rate or respiration of the object to be examined, among the respective time-density curves, are identified as separate groups.

12. The method of claim 1, wherein, during the dividing of the respective individual image points into the plurality of groups of image points, only image points with the assigned intensity values in a value interval are taken into account.

13. The method of claim 12, wherein at least one of:
    the value interval include a range from −50 HU to 150 HU, and
    images recorded in the plurality of bolus-tracking images are registered in sequence.

14. A non-transitory computer readable medium storing a computer program, the computer program being directly loadable into a storage device of a control device of an imaging medical device, the computer program including program segments to cause the control device to execute the method of claim 1 when the computer program is executed by a processor in the control device of the imaging medical device.

15. A non-transitory computer-readable medium, on which computer-executable program segments are stored, for causing a computer to execute the method of claim 1 when the computer-executable program segments are executed by a processor of the computer.

16. An imaging medical device for imaging of a region of interest of an object to be examined, the imaging medical device comprising:
    at least one memory configured to store computer-readable instructions; and
    at least one processor configured to execute the computer-readable instructions to cause the imaging medical device to, receive selection guidelines with respect to selection of a slice of the object to be examined for a plurality of bolus-tracking images, in which a fluid flowing to the region of interest is observable;

actuate an image recording device for taking the plurality of bolus-tracking images of the selected slice over time;

acquire raw data associated with the plurality of bolus-tracking images;

reconstruct image data including intensity values assigned to respective individual image points based on the acquired raw data;

divide the respective individual image points into a plurality of groups of image points according to a similarity of respective time-density curves, the respective time-density curves being determined based on the intensity values assigned to the respective individual image points;

select a first group of image points, for which at least one of the intensity values assigned to the first group of image points is first in time to exceed a threshold intensity value among the intensity values assigned to the respective individual image points, as a reference group of image points from among the plurality of groups of image points;

determine a time, at which the at least one of the intensity values assigned to the reference group of image points exceeds the threshold intensity value, as an initialization time point of the imaging of the region of interest of the object to be examined; and control the image recording device to start the imaging of the region of interest of the object to be examined based on the initialization time point.

17. The imaging medical device of claim 16, comprising:
the image recording device; and
a control device including the at least one memory and the at least one processor of claim 16.

18. The imaging medical device of claim 16, wherein the imaging medical device is a computed tomography system.

* * * * *